US008480752B2

United States Patent
Dun

(10) Patent No.: US 8,480,752 B2
(45) Date of Patent: *Jul. 9, 2013

(54) TIBIAL BEARING HAVING INCREASED AXIAL-ROTATION

(75) Inventor: Shouchen Dun, Fort Wayne, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 828 days.

This patent is subject to a terminal disclaimer.

(21) Appl. No.: 12/165,439

(22) Filed: Jun. 30, 2008

(65) Prior Publication Data

US 2009/0326668 A1    Dec. 31, 2009

(51) Int. Cl.
*A61F 2/38* (2006.01)

(52) U.S. Cl.
USPC .......... 623/20.33; 623/20.15; 623/20.27; 623/20.32

(58) Field of Classification Search
USPC .......... 623/20.14, 20.15, 20.21, 20.27, 20.32, 623/20.33, 20.35, 20.24, 20.26, 20.28
See application file for complete search history.

(56) References Cited

U.S. PATENT DOCUMENTS

| | | | |
|---|---|---|---|
| 4,959,071 A | | 9/1990 | Brown et al. |
| 5,147,405 A | | 9/1992 | Van Zile et al. |
| 5,192,328 A | * | 3/1993 | Winters ............. 623/20.31 |
| 5,370,699 A | | 12/1994 | Hood et al. |
| 6,013,103 A | | 1/2000 | Kaufman |
| 6,080,195 A | * | 6/2000 | Colleran et al. ............. 623/20.32 |
| 6,986,791 B1 | | 1/2006 | Metzger |
| 7,326,252 B2 | | 2/2008 | Otto et al. |
| 2005/0055102 A1 | * | 3/2005 | Tornier et al. ............. 623/20.32 |
| 2006/0265078 A1 | * | 11/2006 | McMinn ............. 623/20.14 |
| 2006/0265080 A1 | * | 11/2006 | McMinn ............. 623/20.27 |

FOREIGN PATENT DOCUMENTS

| | | |
|---|---|---|
| EP | 0970667 | 1/2000 |
| EP | 1378216 | 1/2004 |
| EP | 1400220 | 3/2004 |
| EP | 1591082 | 11/2005 |
| WO | 2004058108 | 7/2004 |

OTHER PUBLICATIONS

European Search Report for European Patent Application No. 09164242.1-2310 / 2140838, Jan. 19, 2010, 10 pgs.
Partial European Search Report for European Patent Application No. 09164242.1-2310, Oct. 19, 2009, 5 pgs.
NexGen Complete Knee Solution Cruciate Retaining Knee (CR), Zimmer, 2 pages, http://www.zimmer.com/z/ctl/op/global/action/1/id/356/template/PC/prcat/P3/prod/y, (2002).

(Continued)

*Primary Examiner* — David H Willse
*Assistant Examiner* — Javier Blanco
(74) *Attorney, Agent, or Firm* — Barnes & Thornburg LLP

(57) ABSTRACT

An orthopaedic prosthesis includes a tibial bearing and a femoral component configured to articulate with the tibial bearing. The tibial bearing and the femoral component are configured to promote outward axial rotation of the femoral component on the tibial component during knee flexion.

5 Claims, 7 Drawing Sheets

OTHER PUBLICATIONS

Advance Stemmed Medical Pivot, Wright Medical Technology, 3 pages, http://www.wmt.com/Downloads/ADVANCE%C2%AE%20Stemmed%20Medial%20Pivot%20broc%20MK419-701.pdf, (2008).

Scorpio NRG, The Evolution in High Performance Knee System, Stryker Orthopaedics, 16 pages, http://www.stryker.com/stellent/groups/public/documents/web_prod/023608.pdf, (2005).

Performance Knee System, BIOMET, 1 page, http://www.biometgermany.de/medhome-uk/knee/primary/performance, (2002).

In Vivo Determination of Posterior Femoral Rollback for Subjects Having a NexGen Posterior Cruciate-Retaining Total Knee Arthroplasty, Bertin et al., (2002), 9 pgs.

Contact stress at the post-cam mechanism in posterior-stabilized total knee arthroplasty, Nakayama et al., (2005), 6 pgs.

Kinematic Comparison Between Mobile-Bearing and Fixed-Bearing Inserts in NexGen Legacy Posterior Stabilized Flex Total Knee Arthroplasty, Shi et al., (2008), 6 pgs.

Stress Analysis of PS Type Knee Prostheses under Deep Flexion, Todo et al., (2007), 9 pgs.

* cited by examiner

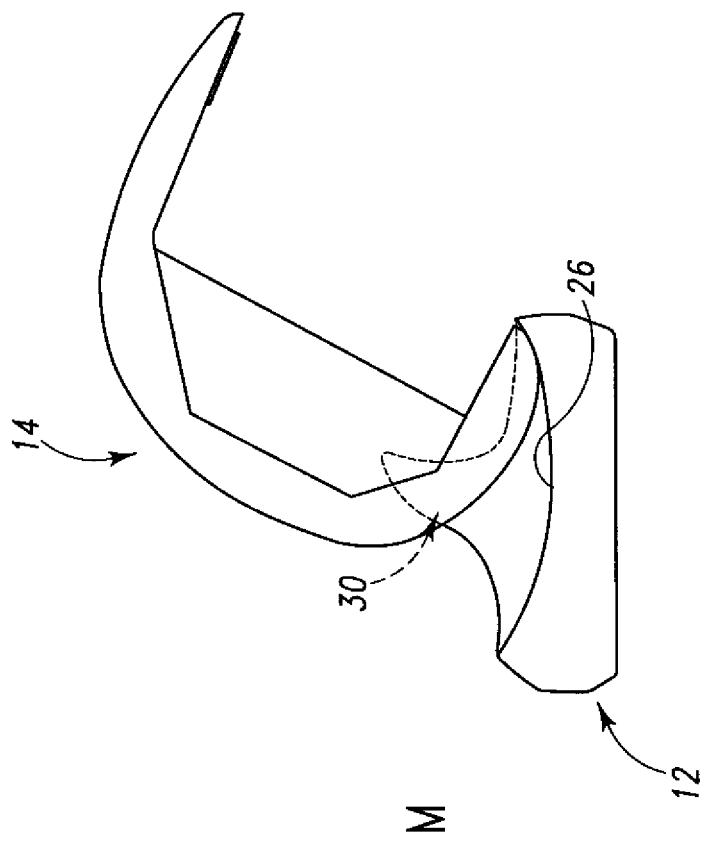
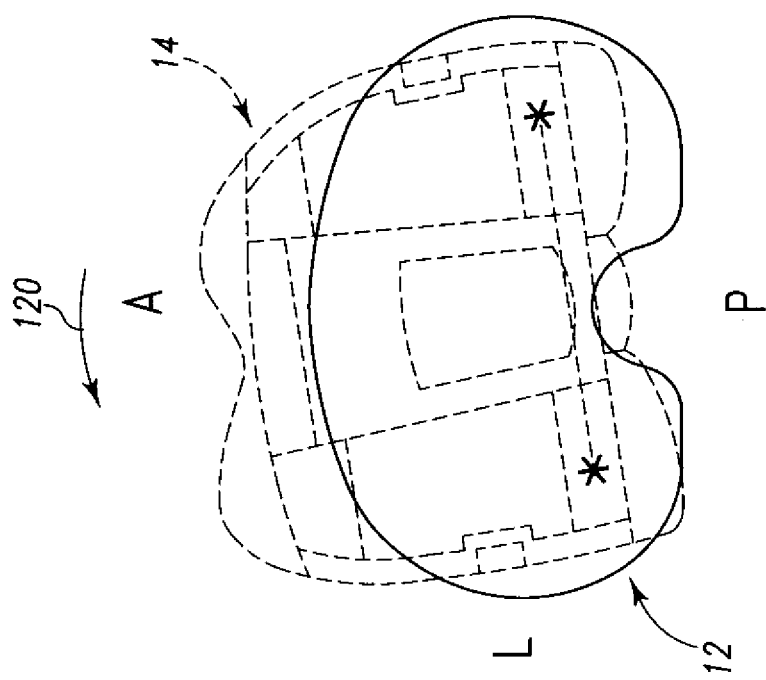

TIBIAL BEARING HAVING INCREASED AXIAL-ROTATION

CROSS-REFERENCE TO RELATED U.S. PATENT APPLICATION

Cross-reference is made to U.S. Utility patent application Ser. No. 12/165,424 entitled "Orthopaedic Knee Prosthesis Having Increased Axial-Rotation" by Shouchen Dun, which was filed on Jun. 30, 2008 and issued as U.S. Pat. No. 8,075,626 on Dec. 13, 2011, the entirety of which is incorporated herein by reference.

TECHNICAL FIELD

The present disclosure relates generally to orthopaedic prostheses, and particularly to posterior stabilized orthopaedic prostheses for use in knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. A knee prosthesis is generally designed to duplicate the natural movement of the patient's joint. However, depending on the severity of the damage to the patient's joint, orthopaedic prostheses of varying mobility may be used. For example, in some patients, the posterior cruciate ligament may be damaged, deficient, or removed during the orthopaedic surgical procedure. In such cases, a posterior stabilized knee orthopaedic prosthesis, which typically restricts or limits the posterior movement of the tibia relative to the femur, may be used.

SUMMARY

According to one aspect of the present disclosure, a tibial bearing of an orthopaedic prosthesis may a platform and a spine. The platform may include a first condylar bearing surface and a second condylar bearing surface. Additionally, the platform may have a centerline axis defined in the anterior-posterior direction when viewed in the transverse plane. The spine may extend upwardly from the platform between the first bearing surface and the second bearing surface. The spine may have a longitudinal axis that is angled with respect to the centerline axis of the platform. In some embodiments, the angle defined between the longitudinal axis of the spine and the centerline axis of the platform is greater than about five degrees. For example, in one particular embodiment, the angle may be about eight degrees; and in another particular embodiment, the angle may be between ten degrees and fifteen degrees.

In some embodiments, the posterior half of the first condylar bearing surface may have a first radius of curvature in the sagittal plane and the posterior half of the second bearing surface may have a second radius of curvature in the sagittal plane. The second radius of curvature may be greater than the first radius of curvature. In some embodiments, the first bearing surface may be embodied as a medial bearing surface and the second bearing surface may be embodied as a lateral bearing surface.

In some embodiments, the spine may include a posterior cam surface. The posterior cam surface may be convex in the transverse plane. Additionally, the posterior cam surface is concave in the sagittal plane.

Further, in some embodiments, the platform may include an anterior rim. Additionally, the spine may include a medial sidewall and a lateral sidewall. In such embodiments, the spine may have a length when viewed in the transverse plane that is defined by a first line segment extending from a medial-lateral center point of the posterior cam surface of the spine to a medial-lateral center point of the anterior rim of the platform. Additionally, the spine may have a first width defined by a second line segment orthogonal to and bisecting the first line segment, the second line segment extending from the medial sidewall to the lateral sidewall of the spine. Further, the spine may have a second width defined by a third line segment orthogonal to the first line segment and crossing the first line segment at a point on the first line segment posterior to the second line segment. The third line segment may extend from the medial sidewall to the lateral sidewall of the spine. The first width of the spine being greater than the second width of the spine. For example, in some embodiments, the first width is greater than the second width by at least 0.5 millimeters. Additionally, in some embodiments the medial sidewall and the lateral sidewall of the spine may taper toward each other in the anterior-posterior direction.

According to another aspect, a tibial bearing may include a platform and a spine. The platform may have a medial bearing surface, a lateral bearing surface, and an anterior rim. The spine may extend upwardly from the platform between the medial bearing surface and the lateral bearing surface. The spine may have a posterior cam surface, a medial sidewall, and a lateral sidewall. Additionally, the spine may have a length when viewed in the transverse plane that is defined by a first line segment extending from a medial-lateral center point of the posterior cam surface of the spine to a medial-lateral center point of the anterior rim of the platform. The spine may also have a first width defined by a second line segment orthogonal to and bisecting the first line segment, the second line segment extending from the medial sidewall to the lateral sidewall of the spine and a second width defined by a third line segment orthogonal to the first line segment and crossing the first line segment at a point on the first line segment posterior to the second line segment. The third line segment may extend from the medial sidewall to the lateral sidewall of the spine. The length of the second line segment may be greater than the length of the first line segment. In some embodiments, the length of the second line segment is greater than the length of the first line segment by at least 0.1 millimeters.

Additionally, in some embodiments, the medial sidewall and the lateral sidewall of the spine may taper toward each other in the anterior-posterior direction. Further, in some embodiments, the platform may have a centerline axis defined in the anterior-posterior direction when viewed in the transverse plane and the spine may have a longitudinal axis that is angled with respect to the centerline axis of the platform. The posterior half of the medial condylar bearing surface in the sagittal plane may have a first radius of curvature and the posterior half of the lateral bearing surface in the sagittal plane may have a second radius of curvature greater than the first radius of curvature. Additionally, in some embodiments, the posterior cam surface of the spine may be convex in the transverse plane. For example, the posterior cam surface of the spine may be concave in the sagittal plane.

According to yet a further aspect, a tibial bearing of an orthopaedic knee prosthesis may include a platform and a spine. The platform may have a medial condylar bearing surface and a lateral condylar bearing surface. The posterior half of the medial condylar bearing surface may have a first radius of curvature in the sagittal plane and the posterior half of the lateral condylar bearing surface may have a second radius of curvature in the sagittal plane that is greater than the first radius of curvature. The spine may extend upwardly from the platform. The spine may have a longitudinal axis that is angled with respect to a centerline of the platform defined in the anterior-posterior direction when the tibial bearing is viewed in the transverse plane. The spine may also have a posterior cam surface that is convex in the transverse plane.

BRIEF DESCRIPTION OF THE DRAWINGS

The detailed description particularly refers to the accompanying figures in which:

FIG. 11 is a schematic diagram of a superior plan view of the assembled orthopaedic knee prosthesis of FIG. 9 positioned in deep flexion; and FIG. 12 is a side elevational view of the assembled orthopaedic knee prosthesis of FIG. 11.

DETAILED DESCRIPTION OF THE DRAWINGS

Figure 1:
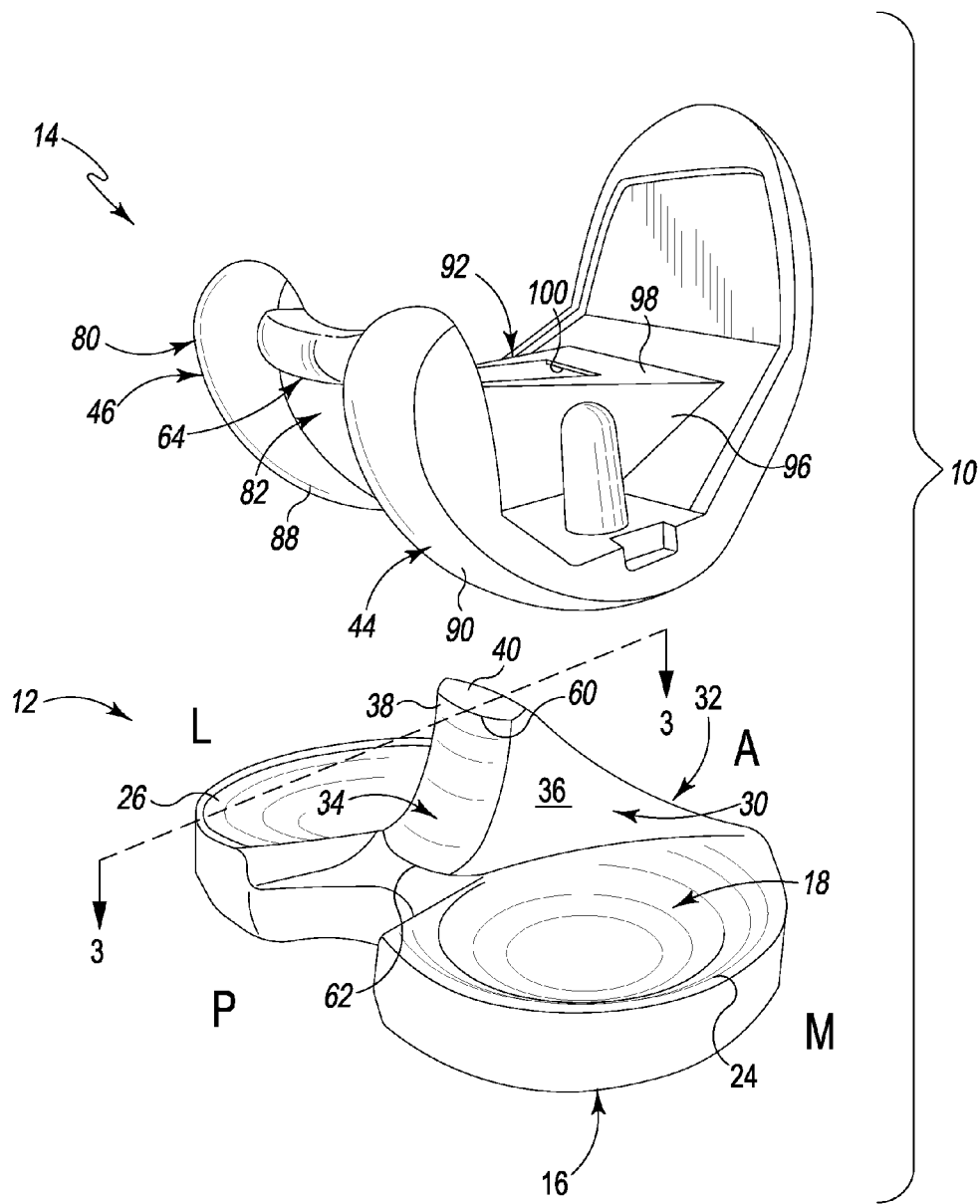
FIG. 1 is a perspective view of one embodiment of an orthopaedic knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, a posterior stabilized orthopaedic knee prosthesis 10 includes a tibial insert or bearing 12, a femoral component 14, and, in some embodiments, a tibial tray (not shown). The femoral component 14 is configured to articulate with the tibial bearing 12 during use. In particular, the knee prosthesis 10 is configured to promote external axial rotation of the femoral component 14 with respect to the tibial bearing 12 during flexion of a patient's knee as discussed in more detail below.

It should be appreciated that the orthopaedic knee prosthesis 10 is illustrated as and discussed below in regard to a left knee prosthesis, which is configured to replace the left knee of a patient. However, in other embodiments, the orthopaedic knee prosthesis 10 may be embodied as a right knee prosthesis configured to replace a right knee of a patient. Regardless, it should be appreciated that the concepts and features discussed and illustrated herein are applicable to both left and right knee orthopaedic prostheses.

The tibial bearing 12 is illustratively formed from a polymer material such as ultra-high molecular weight polyethylene (UHMWPE), but may be formed from other materials, such as a ceramic material, a metallic material, a bio-engineered material, or the like, in other embodiments. Additionally, in the illustrative embodiment, the tibial bearing 12 is embodied as a fixed tibial bearing which may be limited or restricted from rotating relative to the tibial tray.

As shown in FIG. 1, the tibial bearing 12 includes a platform 16 having an upper bearing surface 18 and a bottom surface 20. Illustratively, the bearing 12 may also include other devices or features to secure the tibial bearing 12 to the tibial tray in a non-rotating configuration. The upper bearing surface 18 of the tibial bearing 12 includes a medial bearing surface 24 and a lateral bearing surface 26. The medial and lateral bearing surfaces 24, 26 are configured to receive or otherwise contact corresponding medial and lateral condyles 44, 46 of the femoral component 14, as is discussed in greater detail below. As such, the bearing surfaces 24, 26 may have concave contours in some embodiments.

Figure 2:
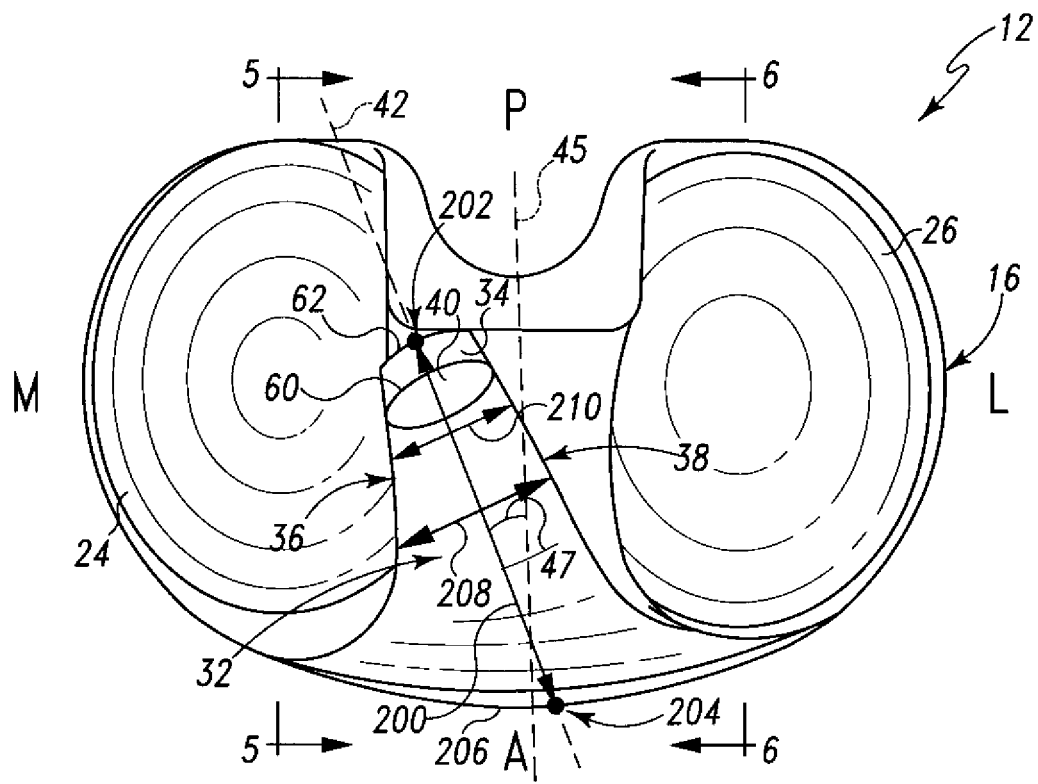
FIG. 2 is a plan view of a tibial bearing of the orthopaedic knee prosthesis of FIG. 1.

A spine 30 of the bearing 12 extends upwardly from the platform 16 and is positioned between the bearing surfaces 24, 26. The spine 30 includes an anterior surface 32, a posterior cam surface 34, a medial sidewall 36, and a lateral sidewall 38. The spine 30 further includes a superior surface 40. Illustratively, as shown in FIG. 2, the spine 30 is angled toward the medial bearing surface 24 of the platform 16 as the spine 30 extends posteriorly. In other words, the spine 30 is angled medially from the anterior surface 32 to the posterior cam surface 34 of the spine 30 in the transverse plane. As such, a longitudinal axis 42 of the spine 30, when viewed in the transverse plane is angled with respect to a centerline axis 45 of the platform 16 extending in the anterior-posterior direction. The longitudinal axis 42 and the centerline axis 45 define an angle 47 therebetween. In some embodiments, spine 30 is configured such that the angle 47 is greater than about five degrees. For example, in one particular embodiment, the angle 47 is about eight degrees. Additionally, in another particular embodiment, the angle 47 is from about ten degrees to about fifteen degrees. However, it is within the scope of this disclosure for the angle between the centerline axes 42, 45 to be any suitable angle. As is discussed in greater detail below, the angle 47 of the spine 30 facilitates outward axial rotation of the femoral component 14 relative to the tibial bearing 12. In particular, the amount of axial rotation of the femoral component 14 is related to the degree or angle 47 of the spine 30. In other words, an increased amount of rotation during flexion of the orthopaedic prosthesis may be obtained by increasing the angle 47 whereas a decreased amount of rotation during flexion may be obtained by decreasing the angle 47.

Referring again to FIG. 2, the spine 30 of the tibial bearing 12 is also tapered in the anterior-posterior direction in the transverse plane. In other words, the medial and lateral surfaces, or sidewalls, 36, 38 of the spine 30 converge toward each other from the anterior surface 32 of the spine 30 to the posterior surface 34 of the spine 30. For example, in some embodiments, the surface 36, 38 may define a respective planes, which taper toward each other and are configured to intersect each other at some location posterior to the spine 30.

As such, the spine 30 may have a substantially decreasing width in the anterior-posterior direction. That is, the spine 30 may have an anterior width that is greater than a posterior width. For example, in one embodiment, the spine 30 may have a length when viewed in the transverse plane defined by a line segment 200 extending from a center point 202 of the posterior cam surface 34 to a center point 204 of an anterior rim 206 of the platform 16. The spine 30 also has an illustrative anterior width defined by a line segment 208 extending from the lateral sidewall 38 to the medial sidewall 36. The line segment 208 is orthogonal to and bisects the line segment 200. The spine 30 also has an illustrative posterior width (with respect as to the anterior width) defined by a line segment 210 extending from the lateral sidewall 38 to the medial sidewall 36. The line segment 210 is orthogonal to the line segment 200 and is positioned posteriorly with respect to the line segment 208. In some embodiments, the anterior width of the spine 30 is greater than the posterior width of the spine 30. That is, the length of the line segment 208 is greater than the length of the line segment 210. For example, in some embodiments, the line segment 208 may have a length that is greater than the length of the line segment 210 by at least 0.1 millimeters. As such, in some embodiments, the spine 30 may be angled and tapered in the anterior-to-posterior direction.

Figure 3:
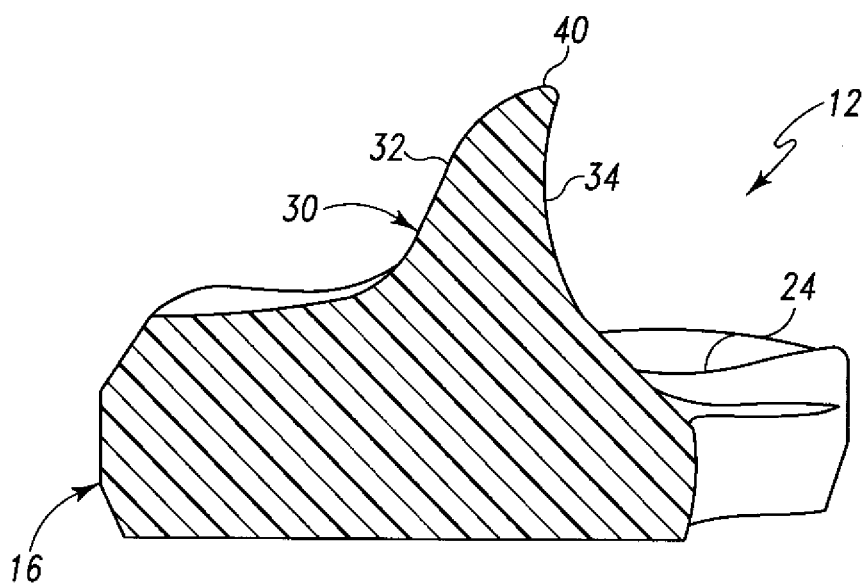
FIG. 3 is a cross-sectional view of the tibial bearing of FIG. 2 taken generally along the line 3-3 of FIG. 1.
Figure 4:
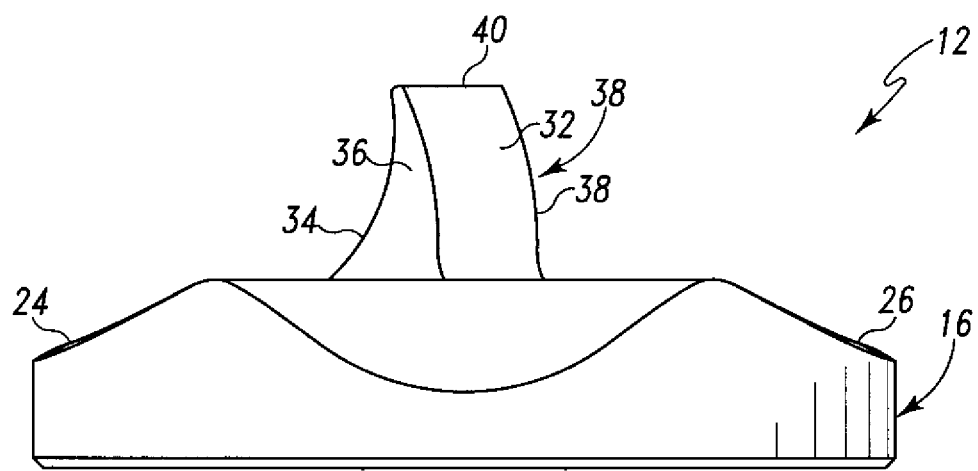
FIG. 4 is an anterior elevational view of the tibial bearing of FIG. 2.

Referring now to FIGS. 2-4, the posterior cam surface 34 of the spine 30 is concave in the sagittal plane (see FIG. 3) and is convex in the transverse plane (see FIG. 2). In other words, as shown in FIG. 2, the posterior cam surface 34 of the spine 30 bows outwardly posteriorly to define a convex superior edge 60 of the posterior surface 34 of the spine 30 and a convex inferior edge 62 of the posterior surface 34 of the spine 30. As is discussed in greater detail below, this posterior bowing of the posterior surface 34 of the spine 30 in the transverse plane also facilitates axial rotation of the femoral component 14 relative to the tibial bearing 12 during flexion as the spine 30 of the tibial bearing 12 interacts with a posterior cam 64 of the femoral component 14. Further illustratively, the outwardly curved posterior surface 34 of the spine 30 may operate to prevent edge loading during axial rotation of the femoral component 14 relative to the tibial bearing 12.

Figure 6:
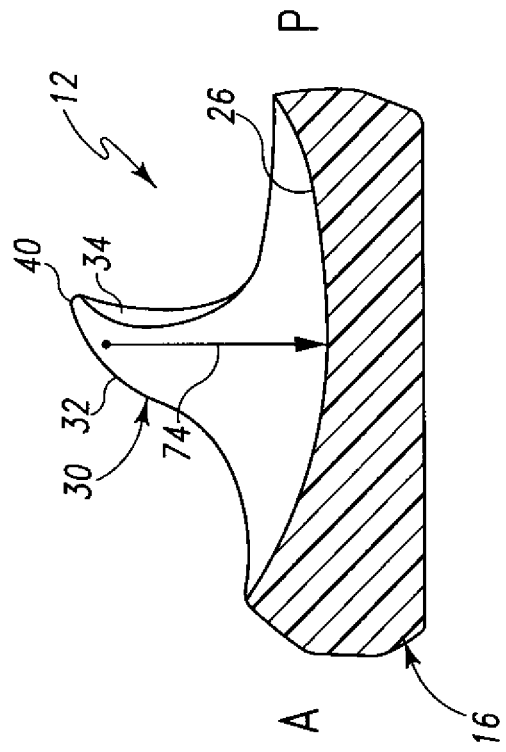
FIG. 6 is another cross-sectional view of the tibial bearing of FIG. 2 taken generally along the line 6-6.
Figure 5:
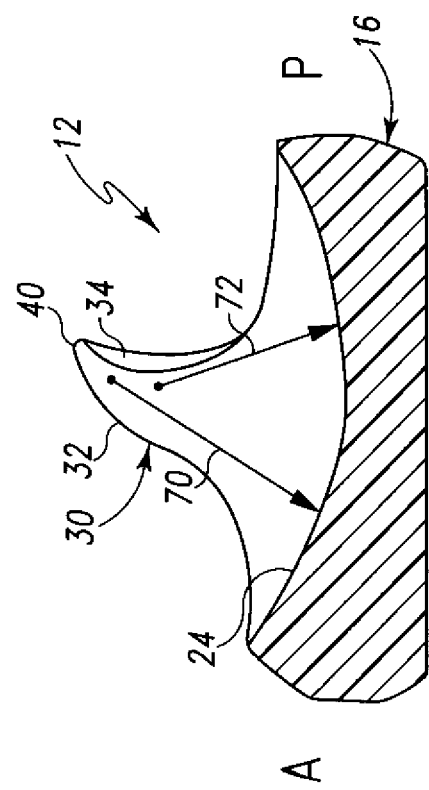
FIG. 5 is a cross-sectional view of the tibial bearing of FIG. 2 taken generally along the line 5-5.

Referring now to FIGS. 5 and 6, the medial condylar bearing surface 24 and the lateral condylar bearing surface 26 of the platform 16 are concavely curved in the sagittal plane. In some embodiments, the lateral condylar bearing surface 26 is less constrained in the posterior region of the surface 26 with respect to the medial condylar bearing surface 24. For example, as shown in FIG. 5, the medial bearing surface 24 in the sagittal plane may be defined by a first radius of curvature 70. Additionally, in some embodiments, the posterior half of the medial bearing surface 24 in the sagittal plane may be defined by a second radius of curvature 72. However, it should be appreciated that while two radii of curvature 70, 72 are disclosed, it is within the scope of this disclosure to provide a lateral medial surface 24 defined by a single radius of curvature or by any suitable number of radii of curvature. Illustratively, the second radius of curvature 72 is smaller than the first radius of curvature 70. However, it is within the scope of this disclosure for the anterior and posterior portions of the medial bearing surface to have any suitable radii of curvature.

Further illustratively, as shown in FIG. 6, the lateral bearing surface 26 is defined by a third radius of curvature 74 in the sagittal plane. Illustratively, the posterior and anterior half of the lateral bearing surface 26 in the sagittal plane are defined by the same radius of curvature 74. However, it is within the scope of this disclosure to include a tibial bearing having a lateral bearing surface which defines multiple radii of curvature. Illustratively, the second, posterior radius of curvature 72 of the posterior half of the medial bearing surface 24 is smaller than the third, posterior radius of curvature of the posterior half of the lateral bearing surface 26. The third radius of curvature 74 may be greater than, less than, or generally equal to the first radius of curvature 70 of the medial bearing surface 24. For example, in one embodiment, the radius of curvature 74 is greater than the radius of curvature 70 by at least 0.5 millimeters. However, it is within the scope of this disclosure for the posterior half of the lateral bearing surface 26 to have any suitable radius of curvature greater than the radius of curvature of the posterior half of the medial bearing surface 24. Accordingly, the posterior region of the medial bearing surface 24 is more constrained than a posterior region of the lateral bearing surface 26. As such, the less constrained posterior region of the lateral bearing surface 26 facilitates outward axial rotation of the femoral component 14 in deep or late flexion, as is discussed in greater detail below.

Figure 7:
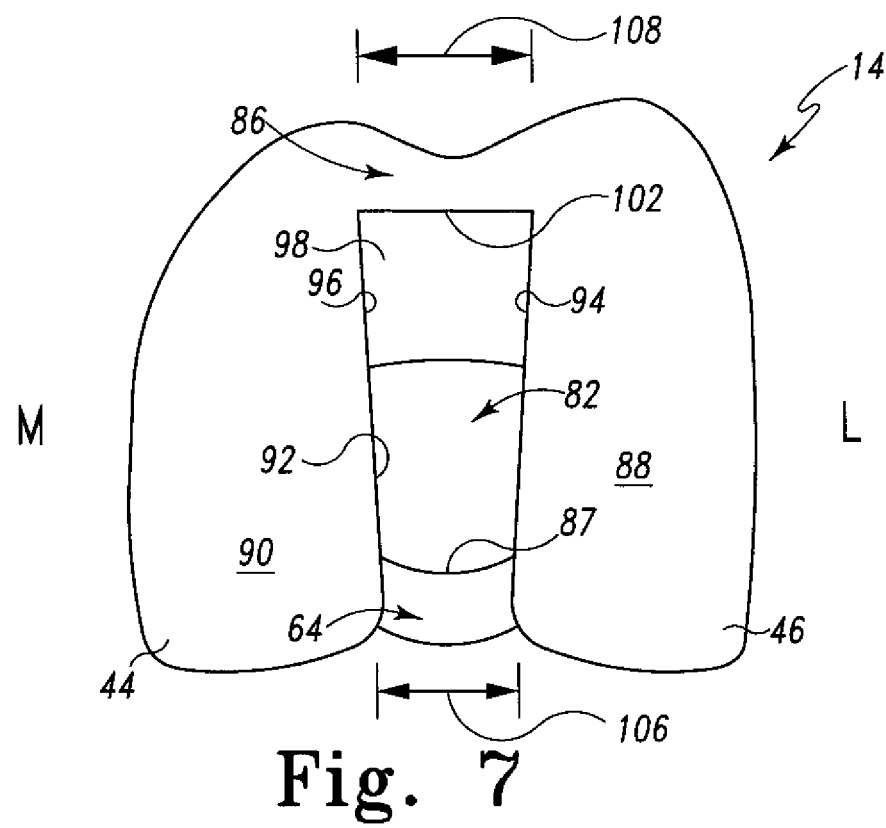
FIG. 7 is an inferior elevational view of a femoral component of the orthopaedic knee prosthesis of FIG. 1.
Figure 8:
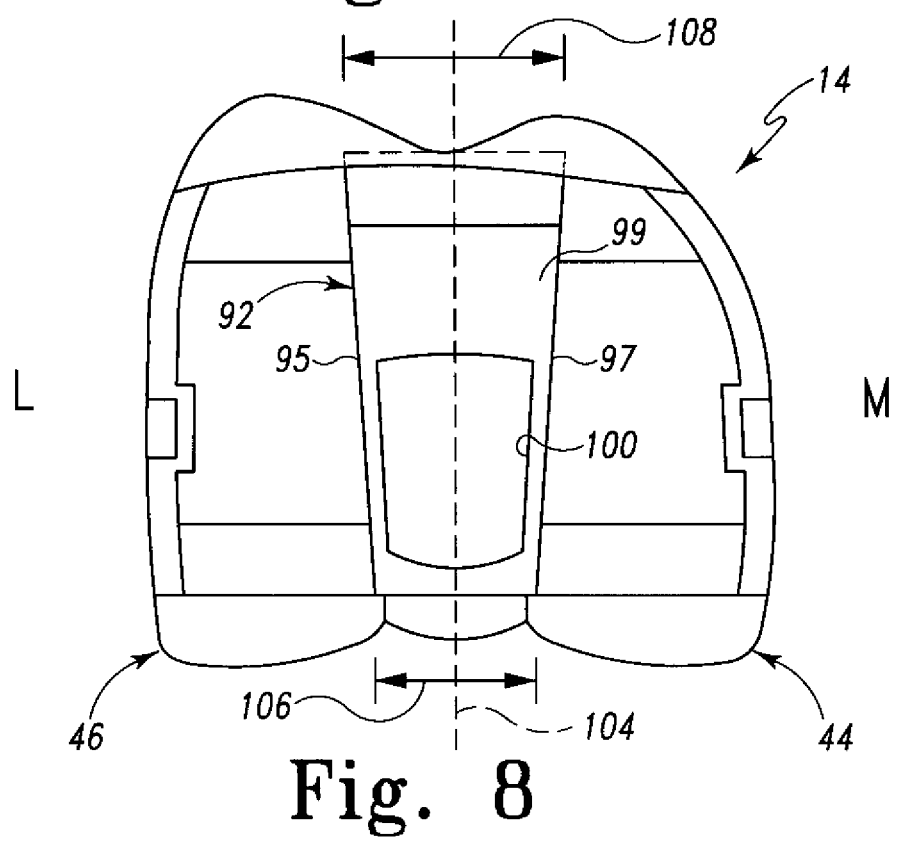
FIG. 8 is a superior elevational view of the femoral component of FIG. 7.

Looking now to FIGS. 7 and 8, the femoral component 14 is configured to be coupled to a surgically-prepared surface of the distal end of a patient's femur (not shown). The femoral component 14 may be secured to the patient's femur via use of bone adhesive or other attachment means. The femoral component 12 is illustratively formed from a metallic material such as cobalt-chromium or titanium, but may be formed from other materials, such as a ceramic material, a polymer material, a bio-engineered material, or the like, in other embodiments.

The femoral component 14 includes an articulating surface 80 having a pair of spaced-apart medial and lateral condyles 44, 46 having respective medial and lateral condyle surfaces 88, 90. In use, the condyles 44, 46 replace the natural condyles of the patient's femur and are configured to articulate on the corresponding bearing surfaces 24, 26 of the platform 16 of the tibial bearing 12.

The condyles 44, 46 are spaced-apart to define an intracondyle notch or recess 82 therebetween. The posterior cam 64 is positioned in the intracondyle notch 82. The posterior cam 64 is located toward the posterior side of the femoral component 14 and includes a cam surface 87 configured to engage or otherwise contact the posterior cam surface 34 of spine 30 of the tibial bearing 12 during flexion as described in more detail below.

Illustratively, the posterior cam surface 87 of the femoral component is concavely curved in the medial-lateral direction as illustrated in FIG. 7. The posterior cam surface 34 of the spine 30 is convex in the traverse plane as illustrated in FIG. 4. Illustratively, the radius of curvature of the cam surfaces 87, 34 may be dependent upon a number of criteria such as the size of the prosthesis, the shape or geometry of the articulating surface of the spine 30 of the tibial implant 12, the shape or geometry of the articulating surface of the cam 64, and/or the like.

The intracondylar notch 82 is defined by a cam box 92. The cam box 92 includes an inner medial wall 96, which is connected to a lateral edge of the medial condyle 90, and an inner lateral wall 94, which is connected to a medial edge of the lateral condyle 88. The cam box 92 also includes an anterior wall 86, which may be embodied as an anterior cam in some embodiments. In such embodiments, the anterior cam includes an anterior cam surface 102. The cam box 92 also includes the posterior cam 64, which forms an inner posterior "wall" of the cam box 92.

The cam box 92 also includes a superior wall 98. Illustratively, the superior wall 98 includes an aperture 100 formed therethrough. The aperture 100 is configured to receive a femoral stem (not shown) to be received with in a bore drilled into the femur of a patient. Additionally, as shown in FIG. 7, the cam box 92 includes an outer medial sidewall 97 and an outer lateral sidewall 95

In embodiments wherein the anterior wall 86 is embodied as an anterior cam, the cam surface 102 may be generally straight in the medial-lateral direction, as shown in FIG. 7. However, it is within the scope of this disclosure to include a curved cam surface as well. Illustratively, the cam surface 102 of the anterior cam 86 may interact with the anterior surface 32 of the spine 30 of the tibial bearing 12 during extension. Further illustratively, although the femoral component includes the cam box 92 having the convex anterior cam 86, it is within the scope of this disclosure to include an anterior cam having another suitable cam surface to interact with the corresponding anterior surface of the spine of the tibial bearing. Further, it is within the scope of this disclosure to provide a cam box without an anterior cam. In other words, it is within the scope of this disclosure to provide a cam box having only a posterior cam, such as the posterior cam 64.

Referring again to FIGS. 7 and 8, the inner medial and lateral sidewalls 96, 94 of the cam box 92 are tapered in the transverse plane. In particular, the sidewalls 94, 96 taper toward each other from the anterior side of the femoral component 14 to the posterior side of the femoral component 14. Accordingly, the medial sidewall 96 is angled with respect to a longitudinal axis 104 of the cam box 92 of the femoral component 14. The lateral sidewall 94 is similarly angled with respect to the longitudinal axis 104 of the cam box 92 of the femoral component 14.

Illustratively, the cam box 92 has a posterior width 106 and an anterior width 108. The posterior width 106 may be equal to a width of the posterior cam 64 between the medial sidewall 96 and the lateral sidewall 94. Similarly, the anterior width 108 may be equal to a width of the anterior wall 86 between the medial sidewall 96 and the lateral sidewall 94. As shown in FIGS. 7 and 8, the anterior width 108 is greater than the posterior width 106. For example, in some embodiments, the anterior width 108 may be greater than the posterior width 106 by 0.5 millimeters or more. However, it is within the scope of this disclosure to include a cam box having any suitable posterior width that is less than the anterior width of the cam box. It is also noted that similar to the spine 30, the distance between the medial and lateral sidewalls 96, 94 of the cam box 92, which is perpendicular to the longitudinal axis 104 of the cam box 92, decreases in a posterior direction.

Illustratively, a medial-lateral width of the cam box 92 between the sidewalls 94, 96 is greater than a medial-lateral width of the spine 30 along similar anterior-posterior positions. In particular, any width of the cam box 92 taken generally in the anterior half of the cam box 92 is wider than the widest portion, i.e., the anterior width 208, of the spine 30. Therefore, the spine 30 generally does not contact the sidewalls 94, 96 of the cam box 92 in early flexion in order to allow the femoral component 14 to remain in a neutral axial position, i.e., having no rotation of the femoral component 14 on the tibial component 12, during early flexion. For example, in some embodiments, the femoral component 14 may remain in a neutral axial position during the first 30 degrees of knee flexion. However, it is within the scope of this disclosure to include a knee prosthesis wherein the femoral component remains in a neutral axial position during any suitable portion of the knee flexion. In other words, it is within the scope of this disclosure to include a knee prosthesis which facilitates the outward axial rotation of the femoral component at some time before or after 30 degrees of knee flexion.

As stated above, the femoral component 14 articulates on the tibial bearing 12 and is urged to rotate outwardly axially in later flexion. Illustratively, as noted above, the angled and tapered spine 30 of the tibial bearing 12 as well as the tapered cam box 92 of the femoral component cooperate to promote outward axial rotation of the femoral component 14 on the tibial bearing 12. Further, the less constrained posterior portion of the lateral bearing surface 26 also promotes such outward axial rotation of the femoral component during flexion. Additionally, the cam surface 34 of the spine 30 is curved posteriorly in the transverse plane and the posterior cam 64 of the femoral component 12 articulates on the cam surfaces 34 in the transverse plane such that rotation of the femoral component 14 about the spine 30 is further facilitated.

Figure 10:
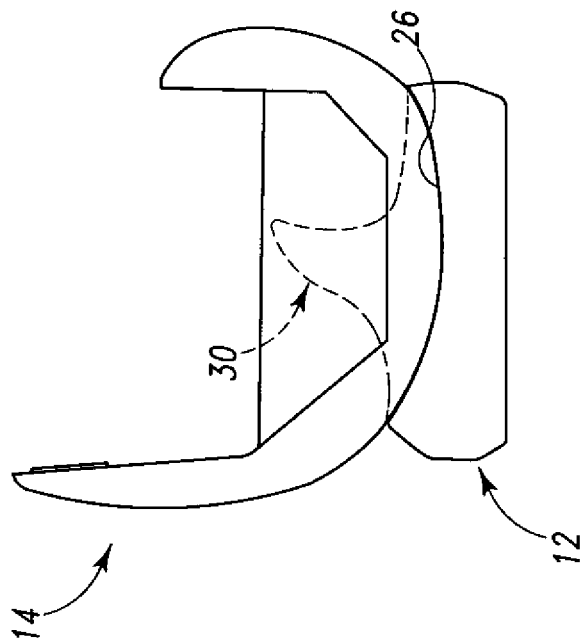
FIG. 10 is a side elevational view of the assembled orthopaedic knee prosthesis of FIG. 9.
Figure 9:
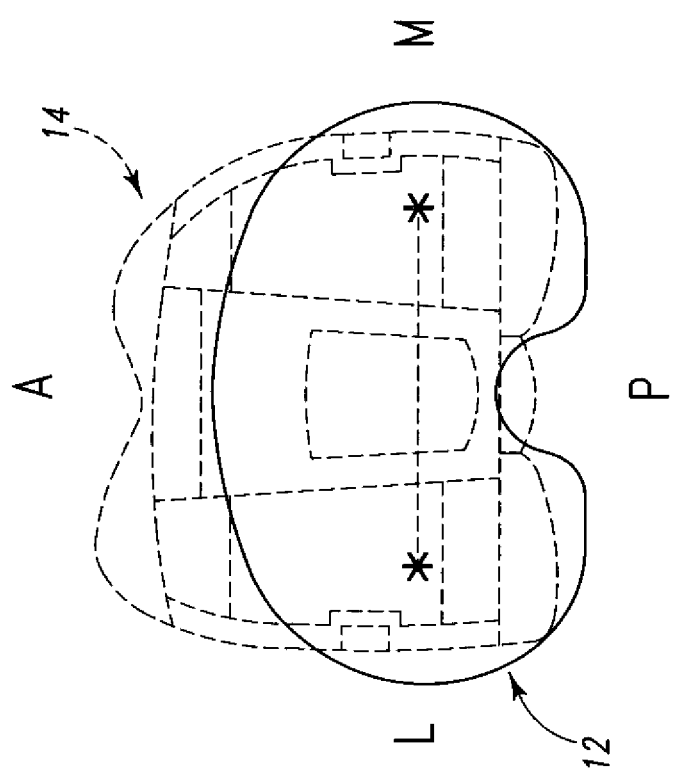
FIG. 9 is a schematic diagram of a superior plan view of the femoral component and tibial bearing of the orthopaedic knee prosthesis of FIG. 1 in an assembled configuration and positioned at about 0 degrees of flexion.

For example, the angled and tapered spine 30 of the tibial bearing 12 cooperates with the tapered cam box 92 during flexion to facilitate axial rotation of the femoral component 14 on the tibial component 12, as shown in FIGS. 11 and 12. Illustratively, the spine 30 is positioned within the intracondyle notch 82, which is substantially defined by the cam box 92, of the femoral component 14. Illustratively, as noted above, the cam box 92 is sufficiently wide to allow the femoral component 14 to stay in a neutral axial position, i.e., having 0 degrees of rotation, relative to the tibial bearing 12, during early knee flexion. For example, as shown in FIGS. 9 and 10, the femoral component 14 is in an axial neutral position at 0 degrees of flexion. This axially neutral position is maintained throughout approximately the first 30 degrees of flexion, as noted above. In other words, the cam box 92 is wide enough to prevent the spine 30 from engaging the sidewalls 94, 96 of the cam box 92 during early flexion.

At approximately 30 degrees of flexion, the sidewalls 94, 96 of the cam box 92 begin to engage with the sidewalls 36, 38 of the spine 30. As such, the angled spine 30 interacts with the cam box 92 to guide the femoral component 14 and axially rotate the femoral component 14 outwardly on the tibial bearing 12. Further illustratively, the tapered sidewalls 36, 38 of the spine 30 and the tapered sidewalls 94, 96 of the cam box 92 cooperate with each other to suitably accommodate the angled spine 30.

Accordingly, the angled spine 30 facilitates rotation of the femoral component 14 outwardly, or in a generally counterclockwise direction 120, as shown in FIG. 11, during later flexion of the knee. As the knee continues to flex, the sidewalls 94, 96 of the cam box 92 and the sidewalls 36, 38 of the spine 30 continue to engage each other resulting in a gradually increased axial rotation of the femoral component 14. As noted below, this process is facilitated by the less-constrained posterior portion of the lateral bearing surface 26 of the tibial bearing 12. The amount of rotation between the femoral component 14 and the tibial bearing 12 during flexion may be adjusted based on the degree of the angle 47 of the spine 30 between the centerline axis of the tibial bearing 45 and the centerline axis of the spine 42. For example, an increased amount of rotation of the femoral component 14 on the tibial bearing 12 may be obtained by increasing the angle 47 of the spine 30.

As noted above, the radii of curvature of the medial and lateral bearing surfaces 24, 26 of the tibial bearing 12 further cooperate with the femoral component 14 to promote the outward axial rotation of the femoral component 14 on the tibial component 12 during flexion. For example, the posterior portion of the lateral bearing surface 26 is less constrained than the posterior portion of the medial bearing surface 24. As discussed above, the posterior radius of curvature 74 of the lateral bearing surface 26 is greater than the posterior radius of curvature 72 of the medial bearing surface 26, thus providing a less constrained posterior bearing surface 26. During later flexion, therefore, the lateral condyle 46 of the femoral component 14 is less constrained within the lateral bearing surface 26 of the tibial bearing 12 when the lateral condyle 46 is engaged with the posterior portion of the lateral bearing surface 26. Accordingly, therefore, the lateral condyle 46 of the femoral component 14 is able to move posteriorly on the lateral bearing surface 26, as shown in deep flexion in FIGS. 11 and 12, to promote the outward axial rotation of the femoral component 14.

As further noted above, the femoral component 14 and the tibial bearing 12 are configured such that the posterior cam 64 of the femoral component 14 contacts the spine 30 of the tibial bearing 12 during flexion. In particular, during flexion, the concave cam surface 87 of the posterior cam 64 of the femoral component 14 contacts the convex cam surface 34 of the spine 30. Accordingly, the interaction between the cam surfaces 34, 87 allows the femoral component 14 to rotate axially relative to the tibial bearing 12 during flexion. In some embodiments, the radius of curvature in the medial-lateral direction of the concave cam surface 87 may be substantially equal to, greater than, or less than the radius of curvature in the transverse plane of the convex cam surface 34 of the spine 30. Illustratively, the concave cam surface 87 of the posterior cam 64 operates to increase the contact area between the posterior surface 34 of the spine 30 and the cam 64. This increase in contact area may decrease the stress between the cam surfaces 34, 87 during axial rotation of the femoral component 14 relative to the tibial bearing 12. Further, the amount of rotation between the femoral component 14 and the tibial bearing 14 during flexion may be adjusted based on the radius of curvatures in the transverse plane of the cam surfaces 34, 87. For example, an increased amount of rotation during flexion of the orthopaedic prosthesis may be obtained by decreasing the radius of curvature in the transverse plane of the convex cam surface 87. Illustratively, while the cam surface 87 of the posterior cam 64 is curved posteriorly, the cam surface 87 may also be substantially planar in the medial-lateral direction in some embodiments.

Illustratively, when the orthopaedic prosthesis 10 is extended or otherwise not in flexion (e.g., a neutral position of about 0 degrees flexion), the posterior cam 64 of the femoral component 14 is not in contact with the spine 30 of the tibial bearing 12. However, late flexion the posterior cam 64 of the femoral component 14 contacts the spine 30 of the tibial bearing 12. Illustratively, for example, in some embodiments, the posterior cam 64 may engage the spine 30 at approximately 70 degrees of flexion. As noted above, during late or deep flexion of the orthopaedic prosthesis 10, the convex cam surface 34 of the spine 30 maintains contact with the concave cam surface 87 of the femoral component 14. It should be appreciated that contact between the posterior cam 64 and the spine 30 is maintained during late flexion.

For example, contact between the concave cam surface 87 of the posterior cam 64 of the femoral component 14 and the convex cam surface 34 of the spine 30 during late flexion may facilitate rollback of the femoral component 14 on the platform 16 of the tibial bearing 12. Furthermore, as noted above, during flexion, the femoral component 14 may rotate about the spine 30 in the generally counter-clockwise or outward axial direction in the transverse plane as indicated by arrow 120 in FIG. 11. The amount of rotation between the femoral component 14 and the tibial bearing 12 during flexion may be adjusted based on the radius of curvatures in the transverse plane of the cam surfaces 34, 87. However, as noted above, the amount of axial rotation of the femoral component 14 relative to the tibial bearing 12 is substantially dependent upon the spine angle 47 and the interaction between the sidewalls 36, 38 of the spine 30 and the sidewalls 94, 96 of the cam box 92.

Illustratively, many features of the prosthesis 10 cooperate to facilitate outward axial rotation of the femoral component 14 on the tibial bearing 12. While these features are shown and described on a common prosthesis 10, it is within the scope of this disclosure to include a knee prosthesis having only one or more of the above-disclosed features which promote the outward axial rotation of the femoral component 14 and which cooperate with and accommodate such features.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. A tibial bearing comprising:
a platform having a medial bearing surface, a lateral bearing surface, and an anterior rim; and
a spine extending upwardly from the platform between the medial bearing surface and the lateral bearing surface, the spine including a posterior cam surface, a medial sidewall, and a lateral sidewall,
wherein the spine has a length when viewed in the transverse plane that is defined by a first line segment extending from a medial-lateral center point of the posterior cam surface of the spine to a medial-lateral center point of the anterior rim of the platform,
wherein the spine has (i) a first width when the tibial bearing is viewed in the transverse plane that is defined by a second line segment orthogonal to and bisecting the first line segment, the second line segment extending from the medial sidewall to the lateral sidewall of the spine and (ii) a second width when the tibial bearing is viewed in the transverse plane that is defined by a third line segment orthogonal to the first line segment and crossing the first line segment at a point on the first line segment posterior to the second line segment, the third line segment extending from the medial sidewall to the lateral sidewall of the spine,
wherein the first width is greater than the second width, and the posterior cam surface of the spine is convex such that when the tibial bearing is viewed in the transverse plane the posterior cam surface bows outwardly posteriorly to define a convex superior edge and a convex inferior edge, and
wherein the platform has a centerline axis defined in the anterior-posterior direction when viewed in the transverse plane, and the spine has a longitudinal axis defined along its length, wherein an angle is defined between the longitudinal axis of the spine and the centerline axis of the platform, when viewed in the transverse plane, and said angle is greater than about five degrees.

2. The tibial bearing of claim 1, wherein the first width is greater than the second width by at least 0.1 millimeters.

3. The tibial bearing of claim 1, wherein the medial sidewall and the lateral sidewall of the spine taper toward each other in the anterior-posterior direction.

4. The tibial bearing of claim 1, wherein:
   (i) the posterior half of the medial condylar bearing surface when the tibial bearing is viewed in the sagittal plane has a first radius of curvature, and
   (ii) the posterior half of the lateral bearing surface when the tibial bearing is viewed in the sagittal plane has a second radius of curvature greater than the first radius of curvature.

5. The tibial bearing of claim 1, wherein the posterior cam surface of the spine is concave in the sagittal plane.

\* \* \* \* \*